United States Patent [19]

Skotheim et al.

[11] Patent Number: 5,089,112
[45] Date of Patent: Feb. 18, 1992

[54] ELECTROCHEMICAL BIOSENSOR BASED ON IMMOBILIZED ENZYMES AND REDOX POLYMERS

[75] Inventors: Terje A. Skotheim, Shoreham, N.Y.; Yoshiyuki Okamoto, Fort Lee, N.J.; Paul D. Hale, Northport, N.Y.

[73] Assignee: Associated Universities, Inc., Washington, D.C.

[21] Appl. No.: 463,540

[22] Filed: Jan. 11, 1990

Related U.S. Application Data

[63] Continuation-in-part of Ser. No. 325,389, Mar. 20, 1989, abandoned.

[51] Int. Cl.⁵ ............................................. G01N 27/26
[52] U.S. Cl. .................................. 204/403; 204/153.12; 435/288; 435/817; 435/176; 435/180; 128/635
[58] Field of Search .................... 204/403, 153.12; 435/288, 817, 176, 180; 128/635

[56] References Cited

U.S. PATENT DOCUMENTS

| | | | |
|---|---|---|---|
| 4,224,125 | 9/1980 | Nakamura et al. | 204/403 |
| 4,321,123 | 3/1982 | Nakamura et al. | 204/403 |
| 4,545,382 | 10/1985 | Higgins et al. | 128/635 |
| 4,704,193 | 11/1987 | Bowers et al. | 204/153.12 |
| 4,711,245 | 12/1987 | Higgins et al. | 128/635 |
| 4,758,323 | 7/1988 | Davis et al. | 204/403 |
| 4,797,181 | 1/1989 | Durfor et al. | 204/153.12 |

OTHER PUBLICATIONS

Biosensors, Chapter 1, Edited by Anthony P. F. Turner et al., Published by Oxford University Press, (1987).
J. Phys. Chem., vol. 91, No. 6, pp. 1285–1289 (1987).
Anal. Chem., vol. 56, pp. 667–671, (1984).
Biosensors, vol. 3, pp. 45–56 (1987/1988).
J. Electroanal. Chem. vol. 250, pp. 417–425 (1988).
J. Am. Chem Soc., vol. 111, pp. 3482–3484 (Apr. 1989).

*Primary Examiner*—John Niebling
*Assistant Examiner*—Arun S. Phasge
*Attorney, Agent, or Firm*—Margaret C. Bogosian

[57] ABSTRACT

The present invention relates to an electrochemical enzyme biosensor for use in liquid mixtures of components for detecting the presence of, or measuring the amount of, one or more select components. The enzyme electrode of the present invention is comprised of an enzyme, an artificial redox compound covalently bound to a flexible polymer backbone and an electron collector.

10 Claims, 2 Drawing Sheets

ELECTROCHEMICAL BIOSENSOR BASED ON IMMOBILIZED ENZYMES AND REDOX POLYMERS

This invention was made with Government support under contract number DE-AC02-76CH00016, between the U.S. Department of Energy and Associated Universities, Inc. The Government has certain rights in the invention.

RELATED APPLICATION

The present application is a continuation-in-part of co-pending U.S. patent application Ser. No. 325,389 filed Mar. 20, 1989, and now abandoned.

BACKGROUND OF THE INVENTION

The present invention relates to an enzyme electrode or electrochemical biosensor, which may be used for electrochemically measuring the concentration of and/or monitoring the level of one or more selected components in a liquid mixture or liquid environment.

These electrochemical biosensors may be used in the chemical, food and biochemical industries and in clinical applications in animal or human medicine, in particular to measure in vivo the concentration of components in body fluids.

These electrochemical biosensors will be described with reference to one particular measurement, the determination of the glucose concentration in an aqueous mixture. While the measurement of glucose concentration is one object of the invention, other and broader objects are not hereby excluded.

Typical amperometric glucose electrodes based on glucose oxidase (GO) undergo several chemical or electrochemical steps which produce a measurable current which is linearly related to the glucose concentration. In the initial step, glucose converts the oxidized flavin adenine dinucleotide (FAD) center of the enzyme into its reduced form (FADH$_2$). Because these redox centers are located well within the enzyme molecule, direct electron transfer to the surface of a conventional electrode does not occur to any measurable degree. A common method of indirectly measuring the amount of reduced glucose oxidase, and hence the amount of glucose present, relies on the natural enzymatic reaction as described in *Biosensors: Fundamentals and Applications* (Oxford University Press, New York, 1987) Chapter 1, and shown by the following reaction formula:

$$\text{glucose} + O_2 \xrightarrow{GO} \text{gluconolactone} + H_2O_2$$

In this reaction, oxygen is the electron acceptor for glucose oxidase. Glucose is oxidized (dehydrogenated) to gluconolactone through the catalytic reaction caused by glucose oxidase, while oxygen is reduced to H$_2$O$_2$. The concentration of O$_2$ and H$_2$O$_2$ can be measured with conventional electrochemical techniques, whereby it is possible to obtain the concentration of glucose indirectly by means of the measurement of O$_2$ consumption as well as H$_2$O$_2$ formation governed by the reaction depicted above. In this measuring scheme the sensor has the disadvantage of being sensitive to the concentration of O$_2$.

Instead of the natural electron acceptor O$_2$, an artificial electron acceptor (mediator) may be used to shuttle electrons between the reduced flavin adenine dinucleotide and the electrode by the following mechanism, described in *Anal. Chem.* 56, 667–671 (1984):

$$\text{glucose} + M_{ox} \xrightarrow{GO} \text{gluconolactone} + M_{red}$$

The preferred mediating species M may be, but is not limited to, ferrocene or a substituted ferrocene.

U.S. Pat. Nos. 4,545,382 and 4,711,245 disclose an enzyme electrode, in which the mediator is a ferrocene or substituted ferrocene molecule. In potential clinical applications, or where long term stability is desirable, sensors based on electron-shuttling redox couples suffer from an inherent drawback: the soluble, or partially soluble, mediating species can diffuse away from the electrode surface into the bulk of the solution. This precludes the use of these devices in implantable probes.

U.S. Pat. No. 4,224,125 discloses an enzyme electrode, in which the water soluble mediator is in polymeric form in order to remain immobilized near the electrode surface by being too large to diffuse through a retaining membrane into the bulk of the solution. The polymeric redox mediator is reduced by the enzyme catalytic process and reoxidized by the electrode, in the vicinity of which it is contained. This electrode design requires a retaining membrane which is a disadvantage for microelectrode applications or where rapid response and high sensitivity are important features of the electrode.

It is desirable to find a mediator which can rapidly transfer electrons between the enzyme and the electrode at a rate corresponding to the rate of the enzyme-catalyzed reaction.

It is further desirable to use a mediating species which is covalently attached in such a fashion as to make it insoluble in the solution to be analyzed, thus preventing the mediating species from diffusing away from the electrode surface.

It is specifically desirable to find a mediator which is relatively insensitive to the presence of interfering substances, in particular oxygen.

These objects are accomplished by the present invention wherein the mediating species is chemically bound to a flexible polymer backbone which allows close contact between the FAD/FADH$_2$ centers of the enzyme and the attached mediator, yet prevents the latter from diffusing away from the electrode surface.

The present invention covers a class of redox polymers which has exceptional properties for mediating enzyme-catalyzed reactions in electrode sensing systems. The redox polymer acts as an electron transfer relay system in a manner similar to that described by Degani and Heller [(*J. Phys. Chem.* 91, 1285–1289 (1987)] where the electron relays are covalently attached to the enzyme itself. A disadvantage of this prior art design is measurably reduced enzyme activity. A further disadvantage is that the applicability of this design is limited to enzymes which allow this particular attachment chemistry. In the present invention, the necessary electrical communication between the FAD/FADH$_2$ centers and the electrode is achieved without modifying the enzyme. A key aspect of the present invention is the use of a highly flexible polymer backbone with sufficient local conformational mobility to allow the attached mediator species to come in close proximity to the enzyme catalytic center, thereby acting as an efficient electron transfer relay to an electron collector. The present system is applicable to all oxidoreductase enzymes, including enzymes which have been modified according to the scheme of Degani and Heller.

One aspect of the invention is to provide a network of donor/acceptor relays covalently attached to a flexible polymer backbone. In another aspect of the invention the flexible polymer backbone is provided by a siloxane polymer. The unique flexibility of the polysiloxane backbone, which has virtually no energy barrier to rotation, allows these relay moieties to interact intimately with the enzyme molecule and achieve a close contact with the FAD/FADH$_2$ centers. This is a vital consideration since, as has been demonstrated [*J. Electroanal. Chem.* 250, 417-425 (1988)], less flexible redox polymers such as poly(vinylferrocene) cannot achieve a sufficiently close contact with the enzyme's redox centers to serve as effective electron transfer relay systems.

An object of the invention is to provide an enzyme electrode for use in liquid mixtures of components for detecting the presence of, measuring the amount of and/or monitoring the level of one or more selected components capable of undergoing an enzyme-catalyzed reaction, in which an oxido-reductase enzyme as well as a polymeric mediator system which transfers electrons to an electron collector when the enzyme is catalytically active, are both maintained in an immobilized state on at least an external surface of the electron collector.

A further object of the invention is to provide an enzyme electrode of the above described type in which the polymeric mediator is comprised of a flexible polymer backbone onto which is covalently attached molecular mediator compounds such as to form a donor-acceptor electron relay system.

A further object of the invention is to provide a polymeric mediator compound which is insoluble in aqueous mixtures such as to remain immobilized on the electrode surface without a retaining membrane.

A further object of the present invention is to provide an enzyme electrode of the above described type which can be formed on a small scale to be used for in vivo concentration measurements.

BRIEF DESCRIPTION OF THE DRAWINGS

The invention will be further described with reference to the accompanying drawings, in which.

DETAILED DESCRIPTION OF THE INVENTION

Figure 1:
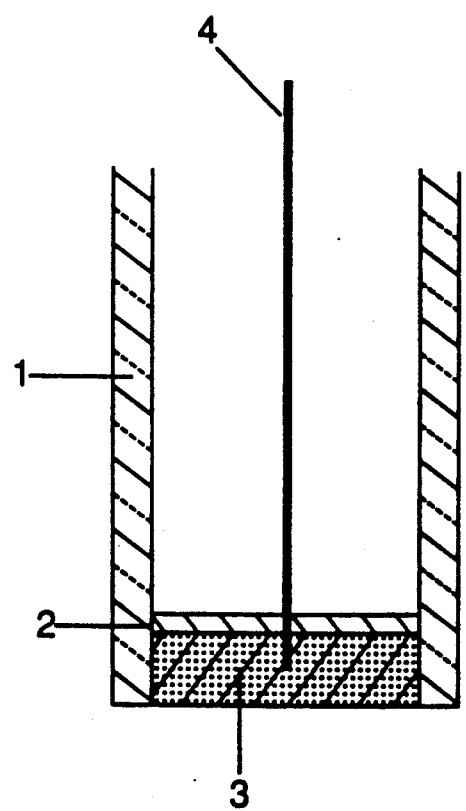
FIG. 1 is a schematic diagram partially showing a longitudinal cross-section of an enzyme electrode according to the present invention.

The electrochemical biosensor of the present invention is characterized by high efficiency for transferring electrons from the reduced enzyme to an electron collector using an artificial redox compound, which functions as a non-physiological electron transfer mediator. The high efficiency derives from the highly flexible polymeric backbone which allows local conformational mobility, thereby providing close proximity to the enzyme redox center of the mediator compounds which are covalently attached to the polymer backbone. The enzyme redox center is located too deep within the enzyme to perform direct electron transfer to a conventional electrode surface.

The preferred polymer backbone is a siloxane polymer, which is characterized by having virtually no energy barrier to rotation, thereby allowing facile local segmental motion. Other examples of flexible polymer backbones are polyphosphazene, poly(ethylene oxide) and poly(propylene oxide).

The preferred mediator compounds are metallocenes, which are organometallic compounds comprising two organic ring structures, each with conjugated unsaturation, and a metal atom sandwiched between the rings, so that the metal atom is in electron-sharing contact with the unsaturated rings.

Ferrocene (dicyclopentadienyl iron), and substituted ferrocene compounds are particularly effective mediators, having pH-independent electrochemically reversible one-electron redox properties, a pH-independent redox potential, slow autoxidation of the reduced form, the absence of any known problems of toxicity or carcinogenicity, a redox potential sufficiently low to avoid excessive interference from competing higher redox potential reactions, satisfactory oxygen insensitivity to avoid excessive interference from oxygen and the ability to be covalently attached to polymer backbones. In a preferred embodiment, no low molecular weight ferrocene specie are present in the polymer since such specie could act as freely diffusing electron transfer mediators.

A further advantage of the ferrocene mediating compounds is the ability to control the redox potential over a wide range through substitution of electron donating or withdrawing groups on the cyclopentadienyl rings. Preferred substituted ferrocenes include, but are not limited to, 1,1'-dimethylferrocene, vinylferrocene, hydroxyethylferrocene, 1,1'-bis(hydroxymethyl)ferrocene, carboxyferrocene, ferrocenylmonocarboxylic acid, 1,1'-dicarboxyferrocene, and trimethylaminoferrocene.

A preferred polymeric mediator system based on a siloxane backbone and attached ferrocene or substituted ferrocene mediator compound is exemplified by the following structural formula:

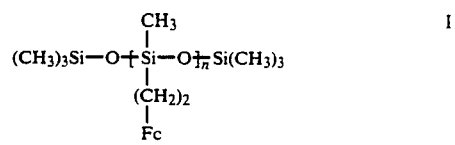

I wherein Fc is ferrocenyl or substituted ferrocenyl, and n = 10 to 50, with n = approximately 35 being preferred.

Other preferred mediator compounds include ruthenocene, dibenzene chromium, phenazine and phenazine derivatives, viologen, riboflavin, p-benzoquinone, and naphthaquinone. In general, redox compounds which can be covalently attached to polymeric backbones and which have redox potentials in the range −0.2 to 0.6 V vs. the Saturated Calomel electrode (SCE) are applicable.

The ferrocene and substituted ferrocene compounds are particularly applicable, as the ferrocenes can mediate electron transfer for a broad range of enzymes.

The preferred enzymes are non-oxygen-specific flavo-protein or quino-protein enzymes, in particular glucose oxidase and glucose dehydrogenase. Other favo-protein enzymes include aldehyde oxidase (aldehydes), glycolate oxidase (glycolate), glutathione reductase (AND(P)H), lactate oxidase (lactate), L-amino acid oxidase (L-amino acids), lipoamide dehydrogenase (NADH), pyruvate oxidase (pyruvate), sarcosine oxidase (sarcosine), choline oxidase (choline) and xanthine oxidase (xanthine), where the substrate to which the enzyme is specific has been denoted in parenthesis.

Other quino-protein enzymes include methylamine dehydrogenase (methylamine) and methanol dehydrogenase (methanol and other alcohols).

Heme-containing enzymes which can be oxidized by ferrocenes include horse-radish peroxidase (hydrogen peroxide), lactate dehydorgenase (lactate) and yeast cytochrome C peroxidase (hydrogen peroxide).

The cupro-protein enzyme galactose oxidase (galactose) and the metalloflavin protein enzyme carbon monoxide oxidoreductase (carbon monoxide) are also applicable.

The enzyme electrodes may be constructed by mixing graphite powder, siloxane-ferrocene polymer and glucose oxidase and blending the resultant mixture into a paste which is subsequently packed into a well at the base of an electrode housing, as shown schematically in FIG. 1.

In order to achieve long term stability, it is advantageous to covalently immobilize the enzyme to the siloxane polymer backbone. This can be achieved with the method described in *Biosensors* 3, 45–56 (1987/88), with amine groups selectively attached to the siloxane backbone on some of the polymer chains or alternately with ferrocenes on the same polymer chain.

The preferred electron collector material is graphite paste due to ease of fabrication and large surface area. Other electrode materials may be silver, platinum, nickel, glassy carbon or tin-oxide.

The manner in which the enzyme electrodes of the present invention are constructed can be understood more fully by reference to the following illustrative examples.

EXAMPLE 1

Glucose oxidase/siloxane-ferrocene polymer

In the following embodiment of the present invention the enzyme was glucose oxidase and the polymer is a siloxane-ferrocene polymer of formula I above wherein Fc is ferrocenyl and n is approximately 35.

This ferrocene-modified siloxane homopolymer was prepared by the hydrosilylation of vinylferrocene with poly(methylhydrosiloxane). Under nitrogen atmosphere, poly(methylhydrosiloxane) (molecular weight 2270) was added into toluene solution of an excess amount of vinylferrocene in the presence of chloroplatinic acid. The reaction mixture was then heated to the reflux temperature. The reaction was allowed to continue until the Si—H IR absorption band disappeared, indicating that all of the starting polymer was converted to product. The resulting ferrocene-modified siloxane polymer was purified by reprecipitation from a chloroform solution via dropwise addition into a large excess of acetonitrile at room temperature. This reprecipitation was repeated until thin layer chromatography showed that no vinylferrocene was present in the precipitate.

Referring to the drawings, FIG. 1 shows the structural details of the enzyme electrode of the present invention. The enzyme electrode comprises a cylindrical electrode holder 1 of an electrically insulating material, an electron collector 2 of carbon formed in a disclike configuration and mounted recessed in the electrode holder 1, a leading wire 4 connected to the electron collector 2, and a carbon paste 3 containing the enzyme-polymer system. The carbon paste was constructed by thoroughly mixing 100 mg of graphite powder with 1 mg of the ferrocene containing polymer, the latter being dissolved in chloroform. After evaporation of the solvent, 10 mg of glucose oxidase (129,000 units/mg) and 20 μl of paraffin oil were added, and the resulting mixture blended into a paste. The paste was packed into a 2 mm deep recess at the base of a glass electrode holder (6 mm inner diameter). For the measurement of the current response the reference electrode was a saturated calomel electrode (SCE) and the auxiliary electrode consisted of a platinum wire. The solutions were deoxygenated with nitrogen prior to each experiment.

Figure 2:
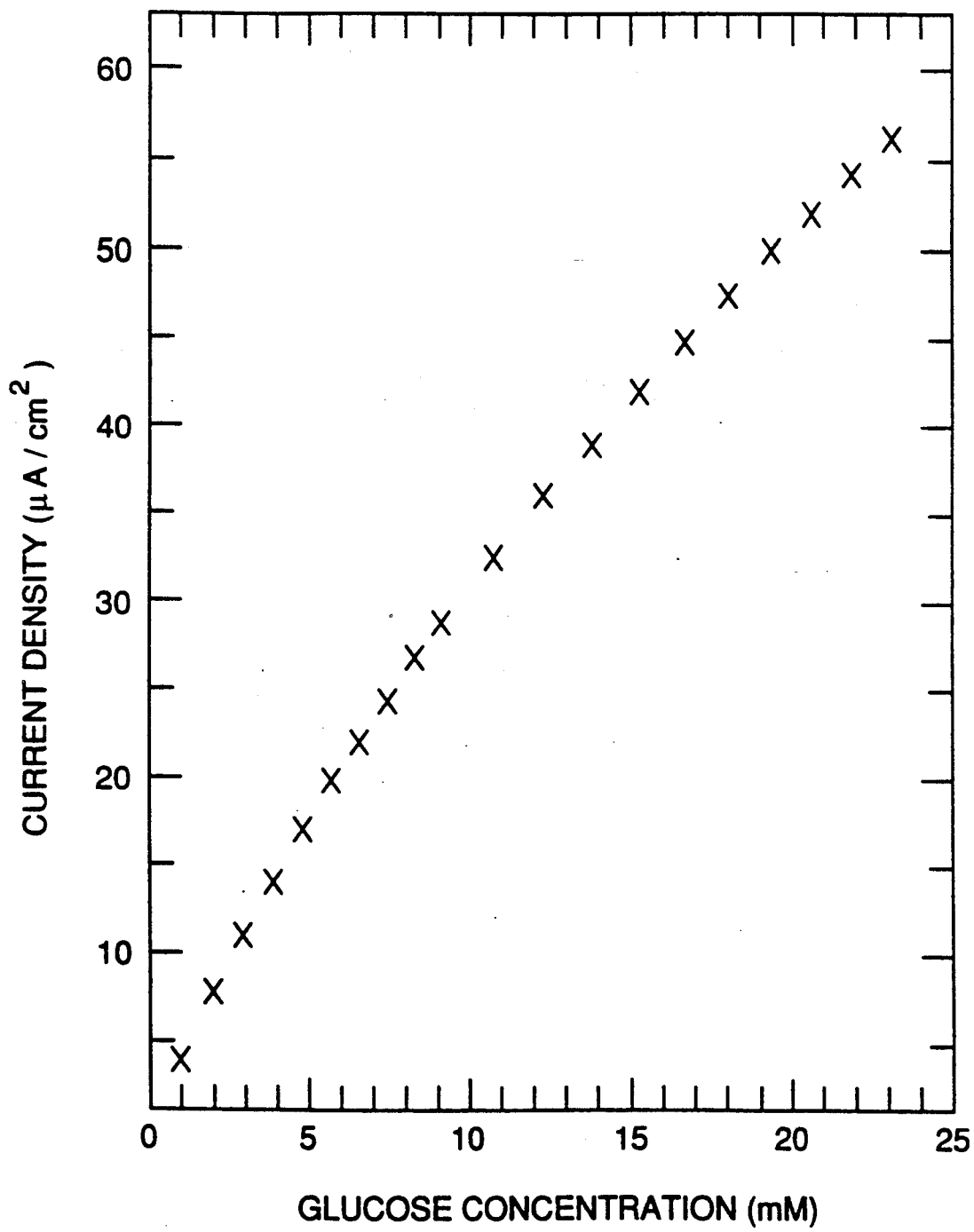
FIG. 2 is a graph showing the current sensed by the electrode of FIG. 1, against glucose concentration.

In FIG. 2, there is shown a current response curve giving the variation of the current measured as a function of the concentration of glucose in a pH 7.0 phosphate buffer solution with 0.1 M KCl added. The enzyme electrode was connected to a potentiostat and maintained at a constant potential of 400 mV vs. the SCE reference electrode. The current produced is proportional to the glucose concentration. The time for 95% of response is approximately 2 minutes.

EXAMPLE 2

Glucose oxidase/siloxane-ferrocene copolymer

In the following embodiment the enzyme was glucose oxidase and the polymer a copolymer having the following structural formula:

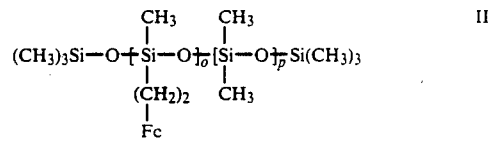

wherein Fc is as defined above, the o:p ratio is approximately 1:2 and $o+p$ is equal to or greater than 10, with the subunits being randomly distributed to form a random block copolymer.

The co-polymer of this embodiment has a lower ferrocene density than the homopolymers of formula 1. The decreased steric hindrance results in a more flexible polymer with more facile local segmental motion to better provide close contact between the ferrocenes and the enzyme redox centers. The experimental results, using glucose oxidase/methyl(ferrocenylethyl)Odimethyl (1:2) siloxane copolymer showed that the increase in current for a specific glucose concentration of $10^{-2}$ mol/1 was 35 μA, which is an improvement over the response in Example 1 by approximately a factor of 3.

EXAMPLE 3

Glycolate oxidase/siloxane-ferrocene polymer

A platinum wire (diameter: 0.01 inch) was dipcoated with the ferrocene-modified siloxane polymer of Example 1 from a solution of 10 mg/ml, then with glycolate oxidase (30 units/ml in pH 8.3 Tris buffer). The current response to sodium glycolate was measured at a potential of 500 mV vs SCE in a solution comprising a phosphate buffer, 0.1 M KCl at pH 8.7. The solution was deaerated with $N_2$. Adding 30 mM sodium glycolate resulted in a current of 0.11 μA.

While particular embodiments of the invention have been described, it will be understood, of course, that the invention is not limited thereto, and that many obvious modifications and variations thereof can be made by those skilled in the art, and that such modifications and variations are intended to fall within the scope of the appended claims.

We claim:

1. An enzyme electrode for sensing the presence of at least one component of a mixture of components, said enzyme electrode comprising:
   (a) an enzyme, the catalytic activity of said enzyme being indicative of said component,
   (b) a non-physiological electron transfer mediator between the enzyme and electron collector, said mediator being covalently attached to an insoluble, flexible siloxane polymer backbone in sufficient number to form an electron relay system,
   (c) and an electron collector,
said enzyme and said mediator-containing siloxane polymer backbone being in an immobilized state in contact with said electron collector.

2. The enzyme electrode of claim 1, wherein the mediator is ferrocene or a substituted ferrocene.

3. The enzyme electrode of claim 2, wherein the mediator is selected from the group consisting of ferrocene, 1,1'-dicarboxyferrocene, carboxyferrocene, vinylferrocene, 1,1'-dimethylferrocene, ferrocenyl-monocarboxylic acid, hydroxyethylferrocene, and 1,1'-bis(hydroxymethyl)ferrocene.

4. The enzyme electrode of claim 1, wherein the enzyme is glucose oxidase.

5. The enzyme electrode of claim 1, wherein the enzyme is glycolate oxidase.

6. The enzyme electrode of claim 1, wherein the mediator is ferrocene, and the enzyme is glucose oxidase.

7. The enzyme electrode of claim 6, wherein the electron collector is composed of graphite powder, and said glucose oxidase, said siloxane and said ferrocene are located on the external surface of said graphite powder.

8. The enzyme electrode of claim 6 having a protective membrane permeable to water and glucose molecules, said membrane covering said external surface of said graphite electron collector.

9. The enzyme electrode of claim 4, wherein the electron collector is composed of platinum or solid carbon.

10. The enzyme electrode of claim 1 comprising means for implantation of said enzyme electrode in a human subject.

* * * * *